United States Patent [19]

Berges

[11] 4,112,086

[45] Sep. 5, 1978

[54] 7β-ACYLAMINO-3-(PHOSPHONOALKYL AND ESTERIFIED PHOSPHONOALKYL SUBSTITUTED TETRAZOLYLTHIOMETHYL)CEPHALOSPORINS

[75] Inventor: David A. Berges, Wayne, Pa.

[73] Assignee: SmithKline Corporation, Philadelphia, Pa.

[21] Appl. No.: 737,971

[22] Filed: Nov. 2, 1976

[51] Int. Cl.$^2$ .................. C07D 501/60; A61K 31/545
[52] U.S. Cl. ...................................... 424/246; 544/21; 544/26; 544/27
[58] Field of Search .................... 260/243 C; 424/250, 424/246; 544/21, 26, 27

[56] References Cited

U.S. PATENT DOCUMENTS

| | | | |
|---|---|---|---|
| 3,883,520 | 5/1975 | DeMarinis | 260/243 C |
| 3,998,817 | 12/1976 | Fukumura et al. | 260/243 C |
| 3,998,821 | 12/1976 | Weir | 260/243 C |
| 4,008,226 | 2/1977 | Sellstedt | 260/243 C |

*Primary Examiner*—Jose Tovar
*Attorney, Agent, or Firm*—Janice E. Williams; William H. Edgerton; Alan D. Lourie

[57] ABSTRACT

The compounds of this invention are cephalosporins having various acylamino substituents at the 7-position and a phosphonoalkyl or esterified phosphonoalkyl substituted tetrazolylthiomethyl group at the 3-position of the cephem nucleus and intermediates for the preparation thereof. The 7-acylated compounds have antibacterial activity.

57 Claims, No Drawings

7β-ACYLAMINO-3-(PHOSPHONOALKYL AND ESTERIFIED PHOSPHONOALKYL SUBSTITUTED TETRAZOLYLTHIOMETHYL)CEPHALOSPORINS

This invention relates to a new series of cephalosporin compounds which have antibacterial activity when administered parenterally and to intermediates for the preparation thereof. In particular, the structures of the biologically active cephalosporin compounds of this invention are characterized by having a phosphonoalkyl or esterified phosphonoalkyl substituted tetrazolylthiomethyl group at the 3-position of the cephem nucleus. Also, this invention extends to methods and compositions for treating certain bacterial infections using these new compounds as well as to certain chemical intermediates and methods for preparing the compounds described hereafter.

The compounds of this invention are represented by the following structural formula:

FORMULA I

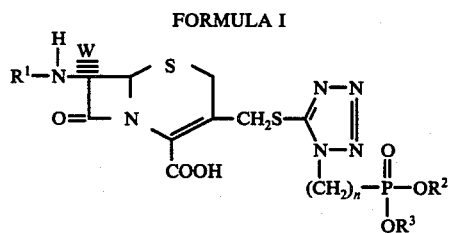

in which:
W is hydrogen or methoxy;
$R^1$ is a pharmaceutically acceptable acyl group known as a 7-substituent in the cephalosporin art;
$R^2$ and $R^3$ are each hydrogen or alkyl of from one to four carbon atoms; and
n is 1 to 5,
or a non-toxic pharmaceutically acceptable salt or hydrate thereof.

Representative of the 7-acyl substituents of the compounds of formula I are those selected from the following group:

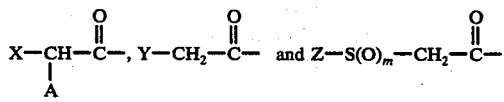

where:
X is thienyl, phenyl or phenyl monosubstituted with hydroxy, hydroxymethyl, formamido or ureido;
A is $NH_2$, OH, COOH, $SO_3H$ or formyloxy;
Y is cyano, sydnone, pyridone, thienyl, tetrazolyl or aminomethylphenyl;
Z is methyl, trifluorometyl, trifluoroethyl, pyridyl or cyanomethyl; and
m is 0 to 2.

A group of compounds of this invention is represented by Formula I where n is 1.

Another group of compounds of Formula I comprises those compounds of Formula I where n is 1 and $R^2$ and $R^3$ are hydrogen.

Yet another group consists of the compounds of Formula I where n is 1, one of $R^2$ and $R^3$ is alkyl and the other is hydrogen.

Still another group consists of the compounds of Formula I where n is 1 and $R^2$ and $R^3$ are both alkyl.

A selected group of the compounds of Formula I are those where n is 1, $R^2$ and $R^3$ are each ethyl or hydrogen, W is hydrogen, $R^1$ is

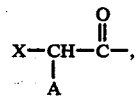

X is phenyl or hydroxyphenyl and A is $NH_2$ or OH.

Some examples of the 7-acyl substituents ($R^1NH—$) of the compounds of Formula I are listed below:

α-hydroxyphenylacetamido
α-aminophenylacetamido
α-amino-4-hydroxyphenylacetamido
trifluoromethylthioacetamido
2,2,2-trifluoroethylsulfinylacetamido
2,2,2-trifluoroethylthioacetamido
cyanoacetamido
α-carboxythienylacetamido
α-carboxyphenylacetamido
α-sulfophenylacetamido
methylsulfonylacetamido
cyanomethylthioacetamido
3-sydnoneacetamido
1-tetrazolylacetamido
2-thienylacetamido
4-pyridylthioacetamido
2-aminomethylphenylacetamido.

Some examples of the compounds of this invention are 7β-D-mandelamino-3-(1-diethoxyphosphinylmethyltetrazol-5-ylthiomethyl)-3-cephem-4-carboxylic acid, 7β-D-mandelamido-3-(1-ethoxyhydroxyphosphinylmethyltetrazol-5-ylthiomethyl)-3-cephem-4-carboxylic acid, 7β-D-mandelamido-3-(1-phosphonomethyltetrazol-5-ylthiomethyl)-3-cephem-4-carboxylic acid, 7β-(2-thienylacetamido)-3-(1-ethoxyhydroxyphosphinylmethyltetrazol-5-ylthiomethyl)-3-cephem-4-carboxylic acid, 7β-(1-tetrazolylacetamido)-3-(1-ethoxyhydroxyphosphinylmethyltetrazol-5-ylthiomethyl)-3-cephem-4-carboxylic acid, 7β-cyanomethylthioacetamido-3-(1-ethoxyhydroxyphosphinylmethyltetrazol-5-ylthiomethyl)-3-cephem-4-carboxylic acid, 7β-(D-α-aminophenylacetamido)-3-(1-ethoxyhydroxyphosphinylmethyltetrazol-5-ylthiomethyl)-3-cephem-4-carboxylic acid, 7β-(D-α-amino-4-hydroxyphenylacetamido)-3-(1-ethoxyhydroxyphosphinylmethyltetrazol-5-ylthiomethyl)-3-cephem-4-carboxylic acid, 7β-D-mandelamino-7α-methoxy-3-(1-phosphonomethyltetrazol-5-ylthiomethyl)-3-cephem-4-cephem-4-carboxylic acid, 7β-(D-α-aminophenylacetamido)-7α-methoxy-3-(1-ethoxyhydroxyphosphinylmethyltetrazol-5-ylthiomethyl)-3-cephem-4-carboxylic acid, 7α-methoxy-7β-trifluoromethylthioacetamido-3-(1-ethoxyhydroxyphosphinylmethyltetrazol-5-ylthiomethyl)-3-cephem-4-carboxylic acid, 7α-methoxy-7β-(2-thienylacetamido)-3-(1-ethoxyhydroxyphosphinylmethyltetrazol-5-ylthiomethyl)-3-cephem-4-carboxylic aicd, 7β-D-mandelamino-7α-methoxy-3-(1-diethoxyphosphinylmethyltetrazol-5-ylthiomethyl)-3-cephem-4-carboxylic acid and 7β-D-mandelamido-7α-methoxy-3-(1-ethoxyhydroxyphosphinylmethyltetrazol-5-ylthiomethyl)-3-cephem-4-carboxylic acid.

It will be recognized that the 4-carboxylic acid group of the compounds of Formula I may be readily esterified by methods well known to the art. These esters include, for example, simple alkyl and aryl esters as well as esters which are easily cleaved, within the body, to the parent acid such as indanyl, pivaloyloxymethyl, acetoxymethyl, propionyloxymethyl, glycyloxymethyl, phenylglycyloxymethyl and thienylglycyloxymethyl esters and others. Of course, when A is COOH, this group may be similarly esterified. All such esters are included within the scope of this invention.

Cephalosporin derivatives having 7-acyl substituents as defined above are well documented in the prior art. Substitution by variously substituted S-heterocyclicthiomethyl-groups, including tetrazolylthiomethyl, at the 3-position of the cephem nucleus is also known. No references to cephalosporin compounds containing the 3-(phosphonoalkyl or esterified phosphonoalkyl substituted tetrazolyl)thiomethyl moiety disclosed herein are believed to be known to the art.

When W is hydrogen, the compounds of Formula I are preferably prepared by acylating 7β-aminocephalosporanic acid (7-ACA) with an appropriate acylating agent, suitably protected as necessary, and then displacing the 3-acetoxy group with the desired phosphonoalkyl or esterified phosphonoalkyltetrazole thiol of the formula:

FORMULA II

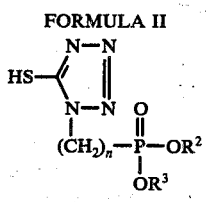

in which:
 n is 1 to 5; and
 $R^2$ and $R^3$ are each hydrogen or alkyl of form one to four carbon atoms, with subsequent removal of the protective group(s). When certain acylating agents are used, for example activated and protected derivatives of mandelic acid, it is preferable to remove the protecting group from the 7-sidechain prior to displacement.

The carboxylic acid group of the acylating agent in the first step of this reaction, the 7-acylation, is activated by any of the standard methods such as conversion to the mixed anhydride, acid chloride, acid imidazolide or activated ester. In addition, a reagent such as dicyclohexylcarbodiimide can be used provided that the carboxyl group on the cephem nucleus is protected with an easily removable protecting group such as a benzhydryl, t-butyl trichloroethyl, benzyl, benzyloxymethyl, p-methoxybenzyl or p-nitrobenzyl ester. When A is $NH_2$, the α-amino group of the acylating agent is, preferably, protected prior to acylation with an easily removable protective group known in the art such as t-butoxycarbonyl, trichloroethoxycarbonyl, benzyloxycarbonyl, the methyl acetoacetate adduct or similar groups commonly used in the synthesis of peptides.

Alternatively, and preferably when W is methoxy, the compounds of Formula I are prepared by acylation as described above, of an appropriate 7β-amino-3-(phosphonoalkyl or esterified phosphonoalkyl substituted tetrazolylthiomethyl)cephalosporin nucleus of Formula III:

FORMULA III

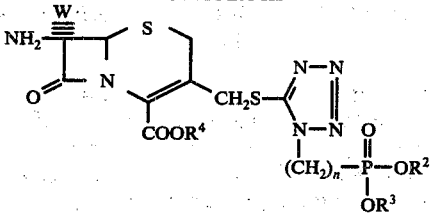

in which:
 W is hydrogen or methoxy;
 n is 1 to 5;
 $R^2$ and $R^3$ are each hydrogen or alkyl of from one to four carbon atoms; and
 $R^4$ is hydrogen or a protecting group, with an appropriate acylating agent followed by removal of the protective groups when present.

The protective groups can be removed accoding to methods well known to the art, such as with trifluoroacetic acid when t-butyl or t-butoxycarbonyl protective groups are used. The resulting salt is converted to the zwitterionic product or to the free acid by means of a basic ion exchange resin such as polystyrene-amine ion exchange resin (for example, Amberlite IR-45) or else by basification of an aqueous solution of the salt.

The acylating agents used as starting materials are either known or prepared by known methods.

The 7β-amino-3-(phosphonoalkyl and esterified phosphonoalkyltetrazolylthiomethyl)cephalosporin starting materials of Formula III where W is hydrogen are prepared by reaction of 7β-aminocephalosporanic acid and a substituted tetrazole thiol of Formula II and then esterifying.

When W is methoxy, the 7β-amino-7α-methoxy cephalosporin nuclei of Formula III are prepared by reaction of the corresponding 7β-amino-3-(substituted tetrazolylthiomethyl)-cephalosporin where W is hydrogen and $R^4$ is a protecting group such as a t-butyl group with 3,5-di-t-butyl-4-hydroxy-benzaldehyde with azeotropic removal of water. Subsequent treatment of the product thus formed with lead dioxide and reaction of the oxidized intermediate with methanol followed by cleavage of the imine function with, for example, Girard reagent T (trimethylaminoacetohydrazide chloride), followed by removal of the protective group(s) as desired gives the compounds of Formula III. When either or both of $R^2$ and $R^3$ are hydrogen, the free hydroxyl group(s) is also protected, for example as a t-butyl ester.

The dialkoxyphosphinylalkyltetrazole thiols of Formula II where $R^2$ and $R^3$ are both alkyl are prepared by reaction of a dialkylphosphinylalkyldithiocarbamate such as methyl 1-(diethoxyphosphinyl)methyldithiocarbamate with an azide such as sodium azide. The dialkoxyphosphinylalkyldithiocarbamates are prepared by treatment of a dialkyl aminoalkylphosphonic acid, for example diethyl aminomethylphosphonate, with carbon disulfide and an alkyl halide such as methyl iodide in the presence of a base such as potassium hyroxide.

The aminoalkylphosphonate dialkyl esters not known to the art are prepared by treatment of a dialkyl phthalimidoalkylphosphonate with hydrazine according to the procedure of Yamauchi et al., *Bull. Chem.*

*Soc. Japan* 48:3285 (1975). The dialkyl phthalimidoalkylphosphonates are prepared via reaction of a N-hydroxyalkylphthalimide with phosphorus tribromide followed by reaction of the N-bromoalkylphthalimide thus formed with a trialkylphosphite as described by Yamauchi et al., *Bull. Chem. Soc. Japan* 45:2531 (1972).

When one of $R^2$ and $R^3$ is hydrogen and the other is alkyl, the alkoxyhydroxyphosphinylalkyltetrazole thiols of Formula II are prepared by basic hydrolysis of the corresponding dialkoxyphosphinylalkyltetrazole thiols.

When $R^2$ and $R^3$ are both hydrogen, the phosphonoalkyltetrazole thiols of Formula II are prepared by treatment of the corresponding dialkoxyphosphinylalkyltetrazole thiols with a mixture of concentrated hydrochloric and acetic acids.

The compounds of Formulas II and III are also considered as objects of this invention.

Certain compounds of this invention are capable of forming salts with, for example, the alkali metals such as sodium or potassium, the alkaline earth metals such as calcium or with the ammonium cation. When A is $NH_2$, the compounds can exist as the zwitterion or as either an acid or base salt. These salts are prepared by standard methods using a wide variety of non-toxic pharmaceutically acceptable acids and bases known in the art and are also considered as objects of this invention.

The compounds of Formula I and salts thereof may also exist as hydrates or solvates. All such hydrates, solvates and fractions thereof are considered as being encompassed within the scope of this invention.

It will be recognized that due to the asymmetric α-carbon atom in the 7-acetamido group of Formula I when

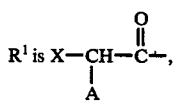

$$R^1 \text{ is } X-\underset{\underset{A}{|}}{CH}-\overset{\overset{O}{\|}}{C}-,$$

optical isomers will exist. Racemic or resolved products are obtained depending upon whether a racemic or resolved sidechain acid is used as an acylating agent. The resolved sidechain acids are readily obtained from the racemic compounds by resolution according to well known methods, including fractional crystallization of a salt formed with an optically active acid or base. All of the isomers, including separated isomers and mixtures thereof, are included within the scope of this invention.

The compounds of Formula I have anti-bacterial activity against both Gram-positive and Gram-negative organisms. Minimum inhibitory concentrations (MIC's) range from 0.1 to >200 µg/ml in in vitro testing. Test results for the compounds 7β-D-mandelamido-3-(1-diethoxyphosphinylmethyltetrazol-5-ylthiomethyl)-3-cephem-4-carboxylic acid sodium salt hydrate (Compound A), 7β-D-mandelamido-3-(1-ethoxyhydroxyphosphinylmethyltetrazol-5-ylthiomethyl)-3-cephem-4-carboxylic acid disodium salt hydrate (Compound B) and 7β-D-mandelamido-3-(1-phosphonomethyltetrazol-5-ylthiomethyl)-3-cephem-4-carboxylic acid (Compound C) are given below. Results shown in parenthesis are those obtained for cefazolin.

| Bacteria | MIC (µg/ml) | | |
|---|---|---|---|
| | Compound A | Compound B | Compound C |
| S. aureus | 3.1, 6.3 (0.4) | 6.3 (0.4) | 6.3 (0.4) |

| Bacteria | MIC (µg/ml) | | |
|---|---|---|---|
| | Compound A | Compound B | Compound C |
| SK 127 | | | |
| S. aureus SK 23390 | 0.8 (0.4) | 1.6 (0.2) | 3.1 (0.2) |
| S. villaluz SK 70390 | 50 (200) | >200 (100) | >200 (200) |
| Strep. faecalis HH 34358 | 12.5 25 (6.3) | 100, 50 (6.3) | 200 (6.3) |
| E. coli SK 12140 | 6.3 (0.8) | 0.4, 0.8 (0.8) | 3.1 (0.8) |
| E. coli HH 33779 | 12.5 (1.6) 6.3 (0.8) | 1.6 (0.8) | 3.1 (0.8) |
| Kleb. pneumo. SK 4200 | 3.1, 1.6 (0.8) | 0.4 (1.6) | 1.6 (0.8) |
| Kleb. pneumo. SK 1200 | 3.1 (1.6) | 0.4 (0.8) | 0.8 (0.4) |
| Salmonella ATCC 12176 | 3.1 (0.8), 1.6 (0.4) | 1.6 (0.8), 0.2 (0.4) | 0.8 (0.4) |
| Pseudo. aerug. HH 63 | >200 (>200) | >200 (>200) | >200 (>200) |
| Serratia marc. ATCC 13880 | 25 (>200), 12.5 (50) | 6.3 (>200), 3.1 (50) | 3.1 (50) |
| Proteus morgani 179 | 3.1 (200), 1.6 (100) | 1.6 (200), 0.1 (100) | 50 (100) |
| Entero. aerog. ATCC 13048 | 12.5 (1.6) | 3.1 (1.6) | 6.3 (1.6) |
| Entero. cloacae HH 31254 | 3.1 (0.8) | 0.8 (0.8) | 1.6 (0.8) |
| Proteus mirabilis 444 | 3.1, 1.6 (3.1) | 1.6 (3.1) | 0.4 (3.1) |

In the in vivo mouse protection test, 7β-D-mandelamido-3-(1-ethoxyhydroxyphosphinylmethyltetrazol-5-ylthiomethyl)-3-cephem-4-carboxylic acid disodium salt hydrate exhibited $ED_{50}$'s at 1.02 mg/kg against *E. coli* 12140 and 0.39 mg/kg against *Kleb. pneumo.* 4200 upon subcutaneous injection; cefazolin gave results of 4.4 mg/kg against *E. coli* 12140 and 7.2 mg/kg against *Kleb. pneumo.* 4200 upon subcutaneous administration.

Pharmaceutical compositions having antibacterial activity which comprise a pharmaceutical carrier containing an active but non-toxic quantity of a compound of Formula I as well as methods of combatting bacterial infections by administering such a composition to an infected host in a non-toxic amount sufficient to combat such infections are also objects of this invention. The administration may be orally or by parenteral injection such as subcutaneously, intramuscularly or intravenously. The injection of suitably prepared sterile solutions or suspensions containing an effective, non-toxic amount of the new cephalosporin compound is the preferred route of administration.

The compounds of Formula I are formulated and administered in the same manner as other cephalosporins. The dosage regimen comprises administration, preferably by injection, of an active but non-toxic quantity of a compound of Formula I selected from the dosage unit range of from 100 to 1000 mg with the total daily dosage regimen being from 400 mg to 6 g. The precise dosages are dependent upon the age and weight of the subject and on the infection being treated and can be determined by those skilled in the art based on the data disclosed herein compared with that available to the art attained with known cephalosporins.

The following examples illustrate the invention but are not to be construed as limiting the scope thereof. Temperatures are in degrees Centigrade (°C.) unless otherwise stated.

EXAMPLE 1

7β-D-Mandelamido-3-(1-diethoxyphosphinylmethyl-tetrazol-5-ylthiomethyl)-3-cephem-4-carboxylic acid Carbon disulfide (0.88 ml, 1.11 g) was added dropwise to a stirred solution of 2.45 g (14.6 mmol) of diethyl aminomethylphosphonate and 0.82 g (14.6 mmol) of potassium hydroxide in 25 ml of ethanol. During addition the temperature of the reaction mixture rose from 26° to 33°. A second portion of 0.88 ml of carbon disulfide was added and the mixture was stirred at 50° for 1 hour. The mixture was cooled to ambient temperature, 2.08 g. (14.6 mmol) of methyl iodide was added dropwise and the resulting mixture was stirred for 1.5 hours. The mixture was evaporated to dryness, the residue was dissolved in water and the aqueous solution was extracted twice with ethyl acetate. The extracts were combined, dried ($MgSO_4$) and evaporated to dryness to give methyl 1-diethoxyphosphinylmethyldithiocarbamate.

To a solution of 2.85 g (11.1 mmol) of methyl 1-diethoxyphosphinylmethyldithiocarbamate in 25 ml of ethanol was added a solution of 0.72 g (11.1 mmol) of sodium azide in 5 ml of water. The reaction mixture was refluxed for 2.5 hours then evaporated to near dryness. Water (20 ml) was added and the aqueous mixture was layered with 40 ml of ethyl acetate and acidified to pH 2.2 by addition of 6N sulfuric acid. The layers were separated and the aqueous phase was extracted twice with ethyl acetate. The ethyl acetate solutions were combined, dried ($MgSO_4$) and evaporated to dryness to give 1-diethoxyphosphinylmethyltetrazole-5-thiol.

$C_6H_{13}N_4O_3PS$. Calculated: 28.5% C; 5.20% H; 22.21% N. Found: 29.39% C; 5.42% H; 22.30% N.

To a solution of 3.42 g (8.0 mmol) of 7-D-mandelamidocephalosporanic acid sodium salt in 75 ml of water was added 2.52 g (10.0 mmol) of 1-diethoxyphosphinylmethyltetrazole-5-thiol and 0.84 g (10.0 mmol) of sodium bicarbonate. The reaction mixture was stirred at ca. 70° for 5.5 hours while maintaining the pH at 7.2. After cooling to ambient temperature the mixture was extracted twice with ether. The aqueous phase was layered with ethyl acetate and acidified to pH 1.9. The layers were separated and the aqueous phase was extracted with ethyl acetate. The ethyl acetate solutions were combined, dried ($MgSO_4$) and evaporated to dryness to give a residue which was dissolved in ethyl acetate. A small volume of ether was added to the ethyl acetate solution and it was filtered. The filtrate was added to 200 ml of rapidly stirring ether and the solid which formed was collected by filtration, dried in vacuo ($P_2O_5$) and chromatographed on silica gel with 90:10:3 chloroform-ethanol-formic acid as eluant to give the title compound.

A solution of 7β-D-mandelamido-3-(1-diethoxyphosphinylmethyltetrazol-5-ylthiomethyl)-3-cephem-4-carboxylic acid in methanol was adjusted to pH 6.5 by addition of 5% aqueous sodium methoxide then filtered. Ether was added to the filtrate and the solid material which formed was collected by filtration to give 7β-D-mandelamido-3-(1-diethoxyphosphinylmethyltetrazol-5-ylthiomethyl)-3-cephem-4-carboxylic acid sodium salt.

$C_{22}H_{26}N_6O_8PS_2 \cdot Na \cdot H_2O$. Calculated: 41.37% C; 4.41% H; 13.16% N. Found: 41.80% C; 4.45% H, 12.48% N.

EXAMPLE 2

7β-D-Mandelamido-3-(1-ethoxyhydroxyphosphinylmethyltetrazol-5-ylthiomethyl)-3-cephem-4-carboxylic acid A solution of 5.04 g (0.02 mol) of 1-diethoxyphosphinylmethyltetrazole-5-thiol in 80 ml of ethanol was treated with 40 ml (0.04 mol) of 1N potassium hydroxide solution and the mixture was refluxed for 1.25 hours. Evaporation of the reaction mixture to dryness gave a residue which was dissolved in 40 ml of 8:2:1 chloroform-ethanol-formic acid. The solid which formed was collected and dissolved in 25 ml of water. The aqueous solution was passed through a column of Dowex 50W-X8 sulfonic acid ion-exchange resin to give, after evaporation of the solvent, a solid material. The solid was dissolved in ether and the ether solution was filtered and evaporated to dryness to give 1-ethoxyhydroxyphosphinylmethyltetrazole-5-thiol, m.p. 119.5–122°.

$C_4H_9N_4O_3PS$. Calculated: 21.43% C; 4.08% H; 24.99% N. Found: 21.15% C; 4.04% H; 24.77% N.

A mixture of 3.42 g (8.0 mmol) of 7β-D-mandelamidocephalosporanic acid sodium salt, 2.5 g (11.2 mmol) of 1-ethoxyhydroxyphosphinylmethyltetrazole-5-thiol and 1.87 g (22.3 mmol) of sodium bicarbonate in 100 ml of water was warmed to 67° and stirred for 4.75 hours while maintaining the pH at 6.9 by addition of sodium bicarbonate. The mixture was cooled to ambient temperature, layered with 100 ml of ethyl acetate and acidified to pH 1.8 with 6N sulfuric acid. The layers were separated and the aqueous phase was extracted with ethyl acetate. The aqueous layer was brought to pH 7 by addition of aqueous sodium bicarbonate and then chromatographed on XAD-7 resin. The eluate was concentrated in vacuo, filtered and lyophilized to give the title compound as the corresponding disodium salt.

$C_{20}H_{21}N_6O_8PS_2 \cdot 2 Na \cdot 3.5 H_2O$. Calculated: 35.45% C; 4.16% H; 12.40% N. Found: 35.17% C; 3.72% H; 12.48% N.

The disodium salt is converted to the title compound by stirring it in aqueous solution with strongly acidic Amberlite IR-120H ion-exchange resin and then lyophilizing.

EXAMPLE 3

7β-D-Mandelamido-3-(1-phosphonomethyltetrazol-5-ylthiomethyl)-3-cephem-4-carboxylic acid A solution of 4.04 g (0.02 mol) of 1-diethylphosphinylmethyltetrazole-5-thiol in 100 ml of 1:1 acetic acid-concentrated hydrochloric acid was refluxed for ca. 16 hours. The solution was evaporated to give a residue which was chromatographed on cellulose with 90:10 acetonitrile-water as eluant. The product-containing fractions were combined and evaporated to a small volume and this solution was passed through a Dowex 50W-X8 sulfonic acid ion-exchange resin column to give 1-phosphonomethyltetrazole-5-thiol, m.p. 185°–186° (dec.)

$C_2H_5N_4O_3PS$. Calculated: 12.25% C; 2.57% H; 28.57% N. Found: 12.66% C; 2.60% H; 28.15% N.

A mixture of 1.92 g (45 mmol) of 7-D-mandelamidocephalosporanic acid sodium salt, 1.2 g (61 mmol) of 1-phosphonomethyltetrazole-5-thiol, 1.01 g (120 mmol) of sodium bicarbonate and 50 ml of water was treated with sufficient 5% aqueous sodium bicarbonate solution to give a pH of 6.9 and then heated at 67° with stirring for 4 hours. The reaction mixture was passed through a XAD-7 ion-exchange resin column and the product-containing fractions were combined and treated with Dowex 50W-X8 sulfonic acid ion-exchange resin in water to bring the pH to 1.4. The resin was filtered off and the solvents were removed. The residue was dissolved in 75:25 acetonitrile-water and passed through a column of microcrystalline cellulose. The product-containing fractions were combined and evaporated to dryness. The residue was dissolved in methanol and Dowex 50W-X8 resin was added until PH 1.6. The resin was filtered off and the remaining solution was cooled in ice and brought to pH 7.0 by addition of a 5% solution of sodium methoxide in methanol. Ether was added with stirring and the resulting solid material was collected by filtration, dissolved in water and lyophilized to give the title compound as its disodium salt.

$C_{18}H_{17}N_6O_8PS_2 \cdot 2$ Na $\cdot$ 2.5 $H_2O$. Calculated: 34.23% C; 3.41% H; 13.30% N; 7.28% Na. Found: 34.65% C; 3.52% H; 12.47% N; 7.49% Na.

7β-D-Mandelamido-3-(1-phosphonomethyltetrazol-5-ylthiomethyl)-3-cephem-4-carboxylic acid disodium salt was converted to the title compound as described in Example 2.

EXAMPLE 4

7β-(D-Aminophenylacetamido)-3-(1-ethoxyhydroxyphosphinylmethyltetrazol-5-ylthiomethyl)-3-cephem-4-carboxylic acid A solution of 7.58 g (0.015 mol) of 7β-(D-α-t-butoxycarbonylaminophenylacetamido)cephalosporanic acid, 2.24 g (0.01 mol) of 1-ethoxyhydroxyphosphinylmethyltetrazole-5-thiol and 2.94 g (0.035 mol) of sodium bicarbonate in 125 ml of water is stirred at 60° for 5 hours while maintaining the pH at 7.0-7.2 by addition of sodium bicarbonate. The mixture is cooled, acidified to pH 3 with dilute hydrochloric acid and extracted with ethyl acetate. After adjusting the pH back to 7 with sodium bicarbonate, the aqueous phase is passed through a XAD-7 resin column and the product-containing fractions are lyophilized to give 7β-(D-α-t-butoxycarbonylaminophenylacetamido)-3-(1-ethoxyhydroxyphosphinylmethyltetrazol-5-ylthiomethyl)-3-cephem-4-carboxylic acid sodium salt.

7β-(D-α-t-Butoxycarbonylaminophenylacetamido)-3-(1-ethoxyhydroxyphosphinylmethyltetrazol-5-ylthiomethyl)-3-cephem-4-carboxylic acid sodium salt (ca. 1 g) is stirred at 25° with 25 ml of trifluoroacetic acid and 25 ml of 1,3-dimethoxybenzene for 2.25 hours. The mixture is evaporated to dryness in vacuo, ether is added to the residue and the precipitate is collected, washed with ether, stirred in acetonitrile for 2 hours and then collected and dried in vacuo to give the title compound as its trifluoroacetic acid salt.

An aqueous solution of the trifluoroacetic acid salt is brought to pH 5.0 by addition of dilute aqueous sodium hydroxide. After lyophilization, the lyophilized material is dissolved in methanol and ether is added to precipitate 7β-(D-α-aminophenylacetamido)-3-(1-ethoxyhydroxyphosphinylmethyltetrazol-5-ylthiomethyl)-3-cephem-4-carboxylic acid sodium salt. The sodium salt is dissolved in water and aqueous solution is passed through an Amberlite IR-120H ion-exchange resin column. Lyophilization of the eluted material gives the title compound.

EXAMPLE 5

Reaction of the N-t-butoxycarbonyl derivative of the following cephalosporanic acids:

7β-(α-amino-4-hydroxyphenylacetamido)cephalosporanic acid
7β-(α-amino-4-formamidophenylacetamido)cephalosporanic acid
7β-(α-amino-3-formamidophenylacetamido)cephalosporanic acid
7β-(α-amino-4-ureidophenylacetamido)cephalosporanic acid
7β-(α-amino-3-ureidophenylacetamido)cephalosporanic acid
7β-(α-amino-4-hydroxymethylphenylacetamido)cephalosporanic acid with 1-ethoxyhydroxyphosphinylmethyltetrazole-5-thiol as described in the procedure of Example 4 followed by removal of the protective group and conversion of the trifluoroacetic acid salt to the free acid as described therein gives the following compounds of this invention:

7β-(α-amino-4-hydroxyphenylacetamido)-3-(1-ethoxyhydroxyphosphinylmethyltetrazol-5-ylthiomethyl)-3-cephem-4-carboxylic acid
7β-(α-amino-4-formamidophenylacetamido)-3-(1-ethoxyhydroxyphosphinylmethyltetrazol-5-ylthiomethyl)-3-cephem-4-carboxylic acid
7β-(α-amino-3-(1-ethoxyhydroxyphosphinylmethyltetrazol-5-ylthiomethyl)-3-cephem-4-carboxylic acid
7β-(α-amino-4-ureidophenylacetamido)-3-(1-ethoxyhydroxyphosphinylmethyltetrazol-5-ylthiomethyl)-3-cephem-4-carboxylic acid
7β-(α-amino-3-ureidophenylacetamido)-3-(1-ethoxyhydroxyphosphinylmethyltetrazol-5-ylthiomethyl)-3-cephem-4-carboxylic acid
7β-(α-amino-4-hydroxymethylphenylacetamido)-3-(1-ethoxyhydroxyphosphinylmethyltetrazol-5-ylthiomethyl)-3-cephem-4-carboxylic acid.

EXAMPLE 6

7β-(4-Hydroxymandelamido)-3-(1-ethoxyhydroxyphosphinylmethyltetrazol-5-ylthiomethyl)-3-cephem-4-carboxylic acid is prepared by reaction of 7β-(4-hydroxymandelamido)cephalosporanic acid sodium salt, 1-ethoxyhydroxyphosphinylmethyltetrazole-5-thiol and sodium bicarbonate as described in the procedure of Example 2 followed by conversion of the product sodium salt to the free acid as described therein.

EXAMPLE 7

When the sodium salt of a cephalosporanic acid listed below:

7β-(3-sydnoneacetamido)cephalosporanic acid
7β-(2-thienylacetamido)cephalosporanic acid
7β-(1-tetrazolylacetamido)cephalosporanic acid is reacted with 1-ethoxyhydroxyphosphinylmethyltetrazole-5-thiol and sodium bicarbonate by the procedure described in Example 2 and the product is converted to the free acid as described therein, the following compounds of this invention are obtained, respectively:

7β-(3-sydnoneacetamido)-3-(1-ethoxyhydroxyphosphinylmethyltetrazol-5-ylthiomethyl)-3-cephem-4-carboxylic acid 7β-(2-thienylacetamido)-3-(1-ethoxyhydroxyphosphinylmethyltetrazol-5-ylthiomethyl)-3-cephem-4-carboxylic acid 7β-(1-tetrazolylacetamido)-3-(1-ethoxyhydroxyphosphinylmethyltetrazol-5-ylthiomethyl)-3-cephem-4-carboxylic acid.

EXAMPLE 8

7β-Trifluoromethylthioacetamido-3-(1-ethoxyhydroxyphosphinylmethyltetrazol-5-ylthiomethyl)-3-cephem-4-carboxylic acid A solution of 2.24 g (10.0 mmol) of 1-ethoxyhydroxyphosphinylmethyltetrazole-5-thiol, 1.68 g sodium bicarbonate and 5.45 g (12.5 mmol) of 7β-trifluoromethylthioacetamidocephalosporanic acid sodium salt in 60 ml of water is stirred at 70°–75° for 5 hours while maintaining the pH at 6.8 by addition of 5% aqueous sodium carbonate solution. The reaction mixture is cooled, acidified to pH 3.0 with dilute hydrochloric acid and extracted with ethyl acetate. After adjusting the pH back to 7 the aqueous phase is passed down an XAD-7 resin column. The product-containing fractions are treated with strongly acidic Amberlite IR-120H ion-exchange resin and then lyophilized to give the title compound.

EXAMPLE 9

Reaction of the sodium salt of a cephalosporanic acid listed below:

7β-(2,2,2-trifluoroethylthioacetamido)cephalosporanic acid

7β-trifluoromethylsulfinylacetamidocephalosporanic acid with 1-ethoxyhydroxyphosphinylmethyltetrazole-5-thiol and sodium bicarbonate as described in the procedure of Example 8 gives the following compounds of this invention as final products:

7β-(2,2,2-trifluoroethylthioacetamido)-3-(1-ethoxyhydroxyphosphinylmethyltetrazol-5-ylthiomethyl)-3-cephem-4-carboxylic acid 7β-trifluoromethylsulfinylacetamido-3-(1-ethoxyhydroxyphosphinylmethyltetrazol-5-ylthiomethyl)-3-cephem-4-carboxylic acid.

EXAMPLE 10

7β-Amino-3-(1-ethoxyhydroxyphosphinylmethyltetrazol-5-ylthiomethyl)-3-cephem-4-carboxylic acid A solution of 13.45 g (0.06 mol) of 1-ethoxyhydroxyphosphinylmethyltetrazole-5-thiol, 10.9 g (0.04 mol) of 7-aminocephalosporanic acid and 13.4 g (0.16 mol) of sodium bicarbonate in 500 ml water is heated at 65° while maintaining the pH at 7.4–7.6 by addition of aqueous sodium carbonate solution. After 3 hours the reaction mixture is cooled to ambient temperature and passed through a column of XAD-7 resin. The product-containing fractions are lyophilized and 7β-amino-3-(1-ethoxyhydroxyphosphinylmethyltetrazol-5-ylthiomethyl)-3-cephem-4-carboxylic acid disodium salt is collected. The disodium salt is converted to the title compound by dissolving in water, adding an amount of trifluoroacetic acid calculated to convert the salt to the acid form, lyophilizing and triturating the lyophilizate with acetone.

EXAMPLE 11

Reaction of 7-aminocephalosporanic acid with 1-diethoxyphosphinylmethyltetrazole-5-thiol and 1-phosphonomethyltetrazole-5-thiol in the presence of 1 and 3 molecular equivalents of sodium bicarbonate, respectively, as described in Example 10 gives 7β-amino-3-(1-diethoxyphosphinylmethyltetrazol-5-ylthiomethyl)-3-cephem-4-carboxylic acid and 7β-amino-3-(1-phosphono-methyltetrazol-5-ylthiomethyl)-3-cephem-4-carboxylic acid, respectively.

EXAMPLE 12

7β-(2,2,2-Trifluoroethylsulfinylacetamido)-3-(1-ethoxyhydroxyphosphinylmethyltetrazol-5-ylthiomethyl)-3-cephem-4-carboxylic acid To a stirred solution of 5.7 g (0.03 mol) of 2,2,2-trifluoroethylsulfinylacetic acid and 3.45 g (0.03 mol) of N-hydroxysuccinimide in 50 ml of tetrahydrofuran at 0° is added 6.2 g (0.031 mol) of dicyclohexylcarbodiimide. The reaction mixture is stirred at 0° for 1 hour then at 25° for 12 hours. The precipitate is filtered and washed with tetrahydrofuran and the filtrate is evaporated to dryness to give the activated ester of 2,2,2-trifluoroethylsulfinylacetic acid.

A suspension of 4.36 g (0.01 mol) of 7β-amino-3-(1-ethoxyhydroxyphosphinylmethyltetrazol-5-ylthiomethyl)-3-cephem-4-carboxylic acid in 50 ml of dry dimethylformamide is treated with 4 ml of triethylamine and the mixture is stirred for 15 minutes at 25°. A slight excess of 0.01 mol of the activated ester of 2,2,2-trifluoroethylsulfinylacetic acid is added to the mixture and it is stirred an additional hour. The reaction mixture is evaporated to dryness and water and ethyl acetate are added to the residue. The layers are separated, the ethyl acetate layer is discarded, fresh ethyl acetate is added to the aqueous phase and it is acidified to pH 2.5 by addition of 6N hydrochloric acid. The mixture is filtered, the layers are separated and the aqueous phase is treated with Amberlite IR-120H ion-exchange resin and lyophilized to give the title compound.

EXAMPLE 13

7β-methylthioacetamido-3-(1-ethoxyhydroxyphosphinylmethyltetrazol-5-ylthiomethyl)-3-cephem-4-carboxylic acid To a stirred, cooled (−20°) solution of 11.34 g (0.026 mol) of 7-amino-3-(1-ethoxyhydroxyphosphinylmethyltetrazol-5-ylthiomethyl)-3-cephem-4-carboxylic acid in 220 ml of 3% sodium bicarbonate and 220 ml of acetone is added dropwise a solution of 3.66 g (0.029 mol) of methylthioacetyl chloride in 52 ml of acetone, during which time the pH of the reaction mixture is maintained at 8.0 by addition of 10% sodium hydroxide. After addition the reaction mixture is stirred an additional 20 minutes at −15°, then is warmed to 25° and extracted with ether. The aqueous phase is passed down a XAD-7 resin column and the product-containing fractions are combined, treated with Amberlite IR-120H ion-exchange resin and lyophilized to yield the title compound.

EXAMPLE 14

7β-(D-α-Formyloxyphenylacetamido)-3-(1-ethoxyhydroxyphosphinylmethyltetrazol-5-ylthiomethyl)-3-cephem-4-carboxylic acid A mixture of 4.36 g (0.01 mol) of 7-amino-3-(1-ethoxyhydroxyphosphinylmethyltetrazol-5-ylthiomethyl)-3-cephem-4-carboxylic acid, 3.97 g (0.02 mol) of the formate ester of D-mandeloyl chloride and 5 g of sodium bicarbonate in 100 ml of water and 140 ml of acetone is stirred in the cold for 1 hour, then at 25° for 2 hours. The acetone is evaporated in vacuo and the remaining aqueous mixture is extracted with ethyl acetate. The aqueous solution is adjusted to pH 7 and passed through a XAD-7 resin column. The product-containing fractions are combined, treated with IR-120H ion-exchange resin and lyophilized to give the title compound.

EXAMPLE 15

Acylation of 7β-amino-3-(1-ethoxyhydroxyphosphinylmethyltetrazol-5-ylthiomethyl)-3-cephem-4-carboxylic acid with an activated derivative of an acid listed below:

cyanoacetic acid
cyanomethylthioacetic acid
4-pyridylthioacetic acid
2-pyridone-N-acetic acid
4-pyridone-N-acetic acid as described in the procedure of Example 12 gives the following compounds of this invention:

7β-cyanoacetamido-3-(1-ethoxyhydroxyphosphinylmethyltetrazol-5-ylthiomethyl)-3cephem-4-carboxylic acid
7β-cyanomethylthioacetamido-3-(1-ethoxyhydroxyphosphinylmethyltetrazol-5-ylthiomethyl)-3-cephem-4-carboxylic acid
7β-(4-pyridylthioacetamido)-3-(1-ethoxyhydroxyphosphinylmethyltetrazol-5-ylthiomethyl)-3-cephem-4-carboxylic acid
7β-(2-pyridoneacetamido)-3-(1-ethoxyhydroxyphosphinylmethyltetrazol-5-ylthiomethyl)-3-cephem-4-carboxylic acid
7β-(4-pyridoneacetamido)-3-(1-ethoxyhydroxyphosphinylmethyltetrazol-5-ylthiomethyl)-3-cephem-4-carboxylic acid.

EXAMPLE 16

Reaction of a cephalosporanic acid listed below or its corresponding salt:

7β-(α-hydroxy-2-thienylacetamido)cephalosporanic acid
7β-(α-carboxy-2-thienylacetamido)cephalosporanic acid
7β-(α-sulfophenylacetamido)cephalosporanic acid with 1-ethoxyhydroxyphosphinylmethyltetrazol-5-thiol and sodium bicarbonate by procedures described hereinabove gives, after conversion of the product to the free acid, the following compounds of this invention:

7β-(α-hydroxy-2-thienylacetamido)-3-(1-ethoxyhydroxyphosphinylmethyltetrazol-5-ylthiomethyl)-3-cephem-4-carboxylic acid
7β-(α-carboxy-2-thienylacetamido)-3-(1-ethoxyhydroxyphosphinylmethyltetrazol-5-ylthiomethyl)-3-cephem-4-carboxylic acid
7β-(α-sulfophenylacetamido)-3-(1-ethoxyhydroxyphosphinylmethyltetrazol-5-ylthiomethyl)-3-cephem-4-carboxylic acid.

EXAMPLE 17

7β-(2,2,2-Trifluoroethylsulfonylacetamido)-3-(1-ethoxy-hydroxyphosphinylmethyltetrazol-5-ylthiomethyl)-3-cephem-4-carboxylic acid To a suspension of 21.8 g (0.05 mol) of 7β-amino-3-(1-ethoxyhydroxyphosphinylmethyltetrazol-5-ylthiomethyl)-3-cephem-4-carboxylic acid in 500 ml of methylene chloride is added over a 30 minute interval a solution of 60.0 g (0.30 mol) of O-t-butyldiisopropylpseudourea in 100 ml of methylene chloride. The mixture is stirred at ambient temperature for 72 hours. The precipitate is removed by filtration and the filtrate is evaporated to a residue which is taken up in 200 ml of benzene and filtered again. The filtrate is extracted with three 100 ml portions of cold 1N hydrochloric acid. The aqueous extracts are layered with ethyl acetate and the pH is adjusted to 7.5 by addition of solid sodium bicarbonate. The organic layer is separated and the aqueous phase is extracted with two 150 ml portions of ethyl acetate. The combined extracts are dried (MgSO$_4$), filtered and evaporated to dryness to give 7β-amino-3-(1-ethoxy-t-butoxyphosphinylmethyltetrazol-5-ylthiomethyl)-3-cephem-4-carboxylic acid t-butyl ester.

To a solution of 10.42 g (0.019 mol) of 7-amino-3-(1-ethoxy-t-butoxyphosphinylmethyltetrazol-5-ylthiomethyl)-3-cephem-4-carboxylic acid t-butyl ester and 3.9 g (0.019 mol) of 2,2,2-trifluoroethylsulfonylacetic acid in tetrahydrofuran is added dropwise a solution of 3.9 g (0.019 mol) of dicyclohexylcarbodiimide in 100 ml of tetrahydrofuran. The reaction mixture is stirred at 25° for 12 hours, then filtered and concentrated to about 10 ml. The residue is filtered and evaporated to dryness to give 7β-(2,2,2-trifluoroethylsulfonylacetamido)-3-(1-ethoxy-t-butoxyphosphinylmethyltetrazol-5-ylthiomethyl)-3-cephem-4-carboxylic acid t-butyl ester.

The ester is dissolved in a 1:3 mixture of 1,3-dimethoxybenzene and trifluoroacetic acid. The solution is stirred for 3 hours and then evaporated to dryness. The resulting residue is triturated with ether to give the title compound.

Likewise, 7β-(2,2,2-trifluoroethylsulfonylacetamido)derivatives of the other 7β-amino-3-substituted tetrazole cephalosporins disclosed herein are prepared.

EXAMPLE 18

7β-D-Mandelamido-3-[1-(2-diethoxyphosphinylethyl)-tetrazol-5-ylthiomethyl]-3-cepham-4-carboxylic acid A mixture of 5.35 g (0.028 mol) of N-(2-hydroxyethyl)phthalimide and 7.7 g (0.028 mol) of phosphorus tribromide is warmed until solution is obtained. The reaction mixture is then cooled and poured into ice water. The resulting solid is collected by filtration and washed with water to give N-(2-bromoethyl)phthalimide.

A mixture of 5.32 g (0.017 mol) of N-(2-bromoethyl)phthalimide and 2.74 g (0.017 mol) of triethyl phosphite is heated gently to initiate reaction. After the reaction subsides, heating is continued for 1 hour with distillation of ethyl bromide. Chloroform is added to the cooled mixture and the solution is washed with water. The organic phase is dried and concentrated to give diethyl phthalimidoethylphosphonate.

A mixture of 4.67 g (0.015 mol) of diethyl phthalimidoethylphosphonate in 30 ml of ethanol and 1.2 ml of 100% hydrazine hydrate is kept at ambient temperature for ca. 16 hours then is refluxed for 2 hours. The mixture is cooled and filtered and the filtrate is concentrated to give diethyl (2-aminoethyl)phosphonate.

Substitution of an equivalent amount of diethyl (2-aminoethyl)phosphonate in place of diethyl aminomethylphosphonate in the procedure of Example 1 followed by cyclization of the dithiocarbamate thus formed gives 1-(2-diethoxyphosphinylethyl)tetrazole-5-thiol.

Reaction of 1-(2-diethoxyphosphinylethyl)-tetrazole-5-thiol with 7-D-mandelamidocephalosporanic acid sodium salt and sodium bicarbonate as described in Example 1 gives 7β-D-mandelamido-3-[1-(2-diethoxyphosphinylethyl)tetrazol-5-ylthiomethyl]-3-cepham-4-carboxylic acid.

EXAMPLE 19

When N-(3-hydroxypropyl)phthalimide is used as a starting material in place of N-(2-hydroxyethyl)phthalimide in the procedure of Example 18, 1-(3-diethoxyphosphinylpropyl)tetrazole-5-thiol is ultimately prepared.

Similarly, when N-(4-hydroxybutyl)phthalimide is used in place of N-(2-hydroxyethyl)phthalimide in the procedure of Example 18, 1-(4-diethoxyphosphinylbutyl)-tetrazole-5-thiol is obtained.

Reaction of 1-(3-diethoxyphosphinylpropyl)tetrazole-5-thiol and 1-(4-diethoxyphosphinylbutyl)tetrazole-5-thiol with 7-D-mandelamidocephalosporanic acid sodium salt and sodium bicarbonate as described in Example 1 gives 7β-D-mandelamido-3-[1-(3-diethoxyphosphinylpropyl)tetrazol-5-ylthiomethyl]-3-cepham-4-carboxylic acid and 7β-D-mandelamido-3-[1-(4-diethoxyphosphinylbutyl)tetrazol-5-ylthiomethyl]-3-cepham-4-carboxylic acid, respectively.

EXAMPLE 20

Reaction of N-bromomethylphthalimide with trimethyl phosphite as described in Example 18 for N-(2-bromoethyl)phthalimide and triethyl phosphite gives dimethyl phthalimidomethylphosphonate.

Treatment of dimethyl phthalimidomethylphosphonate with hydrazine hydrate as described in Example 18 followed by substitution of the dimethyl aminomethylphosphonate thus formed in the procedure of Example 1 in place of diethyl aminomethylphosphonate and subsequent cyclization of the product thus formed gives 1-dimethoxyphosphinylmethyltetrazole-5-thiol.

Reaction of 1-dimethoxyphosphinylmethyltetrazole-5-thiol with 7-D-mandelamidocephalosporanic acid sodium salt and sodium bicarbonate as described in Example 1 gives 7β-D-mandelamido-3-(1-dimethoxyphosphinylmethyltetrazol-5-ylthiomethyl)-3-cephem-4-carboxylic acid.

EXAMPLE 21

Substitution of an equivalent amount of a tetrazole thiol listed below:

1-(2-diethoxyphosphinylethyl)tetrazole-5-thiol
1-(3-diethoxyphosphinylpropyl)tetrazole-5-thiol
1-(4-diethoxyphosphinylbutyl)tetrazole-5-thiol
1-dimethoxyphosphinylmethyltetrazole-5-thiol in the procedure of Example 2 in place of 1-diethoxyphosphinylmethyltetrazole-5-thiol gives the following thiol compounds:

1-(2-ethoxyhydroxyphosphinylethyl)tetrazole-5-thiol
1-(3-ethoxyhydroxyphosphinylpropyl)tetrazole-5-thiol
1-(4-ethoxyhydroxyphosphinylbutyl)tetrazole-5-thiol
1-hydroxymethoxyphosphinylmethyltetrazole-5-thiol.

Reaction of an alkoxyhydroxytetrazole thiol listed above with 7β-D-mandelamidocephalosporanic acid sodium salt as described in Example 2 gives the following compounds of this invention:

7β-D-mandelamido-3-[1-(2-ethoxyhydroxyphosphinylethyl)tetrazol-5-ylthiomethyl]-3-cephem-4-carboxylic acid 7β-D-mandelamido-3-[1-(3-ethoxyhydroxyphosphinylpropyl)tetrazol-5-ylthiomethyl]-3-cephem-4-carboxylic acid 7β-D-mandelamido-3-[1-(4-ethoxyhydroxyphosphinylbutyl)tetrazol-5-ylthiomethyl]-3-cephem-4-carboxylic acid 7β-D-mandelamido-3-(1-hydroxymethoxyphosphinylmethyltetrazol-5-ylthiomethyl)-3-cephem-4-carboxylic acid.

EXAMPLE 22

When a dialkoxyphosphinylalkyl substituted tetrazole thiol listed in Example 21 is used in the procedure of Example 3 in place of 1-diethylphosphinylmethyltetrazole-5-thiol, the following tetrazole thiols are obtained.

1-(2-phosphonoethyl)tetrazole-5-thiol
1-(3-phosphonopropyl)tetrazole-5-thiol
1-(4-phosphonobutyl)tetrazole-5-thiol
1-phosphonomethyltetrazole-5-thiol Reaction of a phosphonoalkyltetrazole-5-thiol listed above with 7β-D-mandelamidocephalosporanic acid sodium salt as described in the procedure of Example 3 gives the following compounds of this invention:

7β-D-mandelamido-3-[1-(2-phosphonoethyl)tetrazol-5-ylthiomethyl]-3-cephem-4-carboxylic acid 7β-D-mandelamido-3-[1-(3-phosphonopropyl)tetrazol-5-ylthiomethyl]-3-cephem-4-carboxylic acid 7β-D-mandelamido-3-[1-(4-phosphonobutyl)tetrazol-5-ylthiomethyl]-3-cephem-4-carboxylic acid 7β-D-mandelamido-3-(1-phosphonomethyltetrazol-5-ylthiomethyl)-3-cephem-4-carboxylic acid.

EXAMPLE 23

7β-Cyanoacetamido-7α-methoxy-3-(1-ethoxyhydroxyphosphinylmethyltetrazol-5-ylthiomethyl)-3-cephem-4-carboxylic acid A solution of 1.32 g (2.4 mol) of 7β-amino-3-(1-ethoxy-t-butoxyphosphinylmethyltetrazol-5-ylthiomethyl)-3-cephem-4-carboxylic acid t-butyl ester and 0.56 g (2.4 mmol) of 3,5-di-t-butyl-4-hydroxybenzaldehyde in 100 ml of dry benzene is refluxed for 4 hours under a Dean-Stark trap. The solution is evaporated under reduced pressure to leave a residue which is dissolved in 100 ml of 1,2-dichloroethane and cooled to ca. 5° in an ice bath. Three grams of freshly prepared lead dioxide is added in portions over 20 minutes until the starting material is completely consumed. The mixture is filtered through Celite and the filter cake is washed with two 20 ml portions of cold 1,2-dichloroethane. The filtrate is treated with 25 ml of methanol (distilled from magnesium) and the reaction mixture is allowed to stand at room temperature until complete consumption of the oxidized intermediate and formation of a new slower-moving product is shown by thin layer chromatography. The mixture is evaporated and the residue is dissolved in 30 ml of methanol and treated with 2.5 g of Girard reagent T (trimethylaminoacetohydrazide chloride). The reaction mixture is stirred at room temperature for 3 hours, then evaporated to give a residue which is partitioned between ethyl acetate and 20% sodium chloride solution. The organic phase is washed with 10% sodium chloride solution and saturated sodium chloride solution. The organic phase is dried (MgSO$_4$), filtered and evaporated to dryness to give 7β-amino-7α-methoxy-3-(1-ethoxy-t-butoxyphosphinylmethyltetrazol-5-ylthiomethyl)-3-cephem-4-carboxylic acid t-butyl ester.

A solution of 2.31 g (4 mmol) of 7⊖-amino-7α-methoxy-3-(1-ethoxy-t-butoxyphosphinylmethyltetrazol-5-ylthiomethyl)-3-cephem-4-carboxylic acid t-butyl ester and 0.60 g (4 mmol) of N,N-diethylaniline in 100 ml of dry methylene chloride is stirred at 0°–5° while 0.41 g (4 mmol) of cyanoacetyl chloride in 20 ml of methylene chloride is added over a 10 minute period. The mixture is stirred in the cold for 30 minutes and then at ambient temperature for an additional 30 minutes. The reaction mixture is washed with 100 ml of dilute hydrochloric acid, 100 ml of 5% sodium bicarbonate and water. The organic phase is dried and evaporated to give a residue which is dissolved in 20 ml of 2:1 trifluoroacetic acid—m-dimethoxybenzene and stirred for 3 hours. Excess trifluoroacetic acid is evaporated and the residue is added to 200 ml of rapidly stirred ether. The resulting precipitate is collected, washed well with ether and dried to give the title compound.

EXAMPLE 24

7β-(D-α-aminophenylacetamido)-7α-methoxy-3-(1-ethoxyhydroxyphosphinylmethyltetrazol-5-ylthiomethyl)-3-cephem-4-carboxylic acid To a solution of 2.31 g (4 mmol) of 7β-amino-7α-methoxy-3-(1-ethoxy-t-butoxyphosphinylmethyltetrazol-5-ylthiomethyl)-3-cephem-4-carboxylic acid t-butyl ester and 1.00 g (4 mmol) of D-α-(N-t-butoxycarbonyl)phenylglycine in 50 ml of dry tetrahydrofuran is added 0.82 g (4 mmol) of dicyclohexylcarbodiimide. The mixture is stirred at ambient temperature for 3 hours. The precipitated urea is removed by filtration and the solvent is evaporated to leave a residue which is taken up in 100 ml of chloroform and washed with 100 ml portions of dilute hydrochloric acid, 5% aqueous sodium bicarbonate and water. The organic layer is separated, dried and evaporated to give a residue which is dissolved in 20 ml of 2:1 trifluoroacetic acid-m-dimethoxybenzene and stirred for 3 hours. Excess trifluoroacetic acid is evaporated under vacuum and the residue is added dropwise to 300 ml of rapidly stirred ether. The precipitate is removed by filtration, washed with ether and dried to give the title compound as its trifluoroacetic acid salt.

An aqueous solution of the trifluoroacetic acid salt is treated with 1 molecular equivalent of sodium bicarbonate and then lyophilized. The lyophilizate is triturated with acetone to give the title compound.

EXAMPLE 25

7β-D-Mandelamido-7α-methoxy-3-(1-ethoxyhydroxyphosphinylmethyltetrazol-5-ylthiomethyl)-3-cephem-4-carboxylic acid A solution of 1.16 g (2 mmol) of 7β-amino-7α-methoxy-3-(1-ethoxy-t-butoxyphosphinylmethyltetrazol-5-ylthiomethyl)-3-cephem-4-carboxylic acid t-butyl ester and 0.30 g (2 mmol) of N,N-diethylaniline in 100 ml of dry methylene chloride is stirred at 0°–5° while 0.56 g (2 mmol) of D-O-dichloroacetylmandeloyl chloride in 10 ml of methylene chloride is added dropwise over 10 minutes. The mixture is stirred in the cold for 30 minutes then warmed to room temperature and stirred for an additional 30 minutes. The solution is washed with 50 ml of cold dilute hydrochloric acid and 50 ml of cold 5% aqueous sodium bicarbonate, dried and evaporated to dryness. The residue is dissolved in a mixture of 10 ml of trifluoroacetic acid and 2 ml of m-dimethoxybenzene and stirred at ambient temperature for 2 hours. The excess trifluoroacetic acid is evaporated under vacuum and the residue is partitioned between 50 ml of ether and 50 ml of water and adjusted to pH 9.3-9.5 with 5% aqueous sodium carbonate. The organic phase is separated and discarded. The aqueous phase is stirred at pH 9.3-9.5 for 30 minutes, layered with ethyl acetate and adjusted to pH 3.0 with dilute hydrochloric acid. After separation of the layers, the aqueous phase is adjusted to pH 7 with sodium bicarbonate and passed through a XAD-7 resin column. The product-containing fractions are combined, stirred with Amberlite IR-120H ion-exchange resin and lyophilized to give the title compound.

EXAMPLE 26

7α-Methoxy-7β-(2-thienylacetamido)-3-(1-ethoxyhydroxyphosphinylmethyltetrazol-5-ylthiomethyl)-3-cephem-4-carboxylic acid A solution of 1.28 g (3 mmol) of 7α-methoxy-7β-(2-thienylacetamido)cephalosporanic acid sodium salt is dissolved in 50 ml of water. 1-Ethoxyhydroxyphosphinylmethyltetrazole-5-thiol (1.12 g, 4.5 mmol) and sufficient sodium bicarbonate to bring the pH to 6.8 are added and the solution is heated at 70° until thin layer chromatography indicates consumption of the starting cephalosporanic acid (ca. 5 hours). After cooling to ambient temperature, the reaction mixture is passed through a XAD-7 resin column and the product-containing fractions are combined, stirred with Amberlite IR-120H ion-exchange resin and lyophilized to give the title compound.

EXAMPLE 27

7α-Methoxy-7β-trifluoromethylthioacetamido-3-(1-ethoxyhydroxyphosphinylmethyltetrazol-5-ylthiomethyl)-3-cephem-4-carboxylic acid To a cold solution of 5.25 g (0.012 mol) of 7β-amino-7α-methoxycephalosporanic acid benzhydryl ester in 200 ml of methylene chloride containing 1.79 g (0.012 mol) of N,N-diethylaniline is added dropwise over a 20 minute period a solution of 1.82 g (0.012 mol) of trifluoromethylthioacetyl chloride in 50 ml of methylene chloride. After stirring for 30 minutes, the mixture is extracted successively with 5% aqueous sodium bicarbonate, 5% aqueous hydrochloric acid and finally with brine. The organic phase is dried (MgSO₄) and the solvent evaporated to give 7α-methoxy-7β-trifluoromethylthioacetamidocephalosporanic acid benzhydryl ester.

7α-Methoxy-7β-trifluoromethylthioacetamidocephalosporanic acid benzhydryl ester is dissolved in a cold mixture of trifluoroacetic acid-anisole (2:1) and the mixture is stirred for 1.5 hours without external cooling. The solvent is evaporated in vacuo and the residual product is taken up in ethyl acetate, washed with water, dried (MgSO₄) and concentrated in vacuo to a small volume. This solution is added dropwise to stirred petroleum ether to yield 7α-methoxy-7β-trifluoromethylthioacetamidocephalosporanic acid.

7α-Methoxy-7β-trifluoromethylthioacetamidocephalosporanic acid (2.2 g, 5 mmol) is suspended in 75 ml of water and 0.4 g of solid sodium bicarbonate is added. To this solution is added 1.7 g (7.5 mmol) of 1-ethoxyhydroxyphosphinylmethyltetrazole-5-thiol and sufficient sodium bicarbonate to bring the pH to 7.5. The mixture is heated at 70° for 7 hours while maintaining the pH at 7.5. Progress of the reaction is monitored by thin layer chromatography and judged to be complete when tlc indicates disappearance of starting material (ca. 7 hours). The reaction mixture is then cooled to ambient temperature and the product-containing fractions are combined, stirred with Amberlite IR-120H ion-exchange resin and lyophilized to give the title compound.

EXAMPLE 28

7β-(2-Aminomethylphenylacetamido)-3-(1-ethoxyhydroxyphosphinylmethyltetrazol-5-ylthiomethyl)-3-cephem-4-carboxylic acid To a stirred solution of 2.65 g (0.01 mol) of 2-(N-t-butoxycarbonylaminomethyl)phenylacetic acid in 75 ml of dry tetrahydrofuran at ca. −10° was added dropwise 1.36 g (0.01 mol) of isobutylchloroformate and 2 drops of methyl morpholine. The reaction mixture was stirred at −10° for 10 minutes then a cooled (0°) solution of 2.72 g (0.01 mol) of 7β-aminocephalosporanic acid in 50 ml of 50% tetrahydrofuran containing 1.01 g of triethylamine was added dropwise while maintaining the temperature at ca. −10°. The mixture was stirred at −15° for 1 hour, then at ambient temperature for 2 hours. The pH was adjusted to 7.5 with sodium bicarbonate and the mixture was extracted repeatedly with ethyl acetate. The extracts were combined, filtered through Celite, dried (MgSO₄) and evaporated to dryness to give 7β-(2-N-t-butoxycarbonylaminomethylphenylacetamido)-cephalosporanic acid.

7β-(2-N-t-Butoxycarbonylaminomethylphenylacetamido)-cephalosporanic acid (7.79 g, 0.015 mol) and 2.24 g (0.01 mol) of 1-ethoxyhydroxyphosphinylmethyltetrazole-5-thiol are suspended in 100 ml of water and sufficient sodium bicarbonate is added to give a solution of pH 7.0. This solution is heated at 60° for 4 hours, cooled to ambient temperature and acidified to pH 3.0 with dilute hydrochloric acid. After extracting with ethyl acetate, the aqueous solution is adjusted to pH 7.0 by addition of sodium bicarbonate and passed through a XAD-7 resin column. The product-containing fractions are lyophilized to give 7β-(2-N-t-butoxycarbonylaminomethylphenylacetamido)-3-(1-ethoxyhydroxyphosphinylmethyltetrazol-5-ylthiomethyl)-3-cephem-4-carboxylic acid disodium salt.

7β-(2-N-t-Butoxycarbonylaminomethylphenylacetamido)-3-(1-ethoxyhydroxyphosphinylmethyltetrazol-5-ylthiomethyl)-3-cephem-4-carboxylic acid disodium salt (ca. 1 g) is stirred at 25° with 25 ml of trifluoroacetic acid and 25 ml of 1,3-dimethoxybenzene for 2.25 hours. The mixture is evaporated to dryness in vacuo, ether is added to the residue and the precipitate is collected, washed with ether, stirred in acetonitrile for 2 hours and then collected and dried in vacuo to give the title compound as its trifluoroacetic acid salt.

An aqueous solution of the trifluoroacetic acid salt is brought to pH 5.0 by addition of dilute aqueous sodium hydroxide. After lyophilization, the lyophilized material is dissolved in methanol and ether is added to precipitate 7β-(2-aminomethylphenylacetamido)-3-(1-ethoxyhydroxyphosphinylmethyltetrazol-5-ylthiomethyl)-3-cephem-4-carboxylic acid sodium salt. The sodium salt is dissolved in water and the aqueous solution is passed through an Amberlite IR-120H ion-exchange resin column. Lyophilization of the eluted material gives the title compound.

EXAMPLE 29

An injectable pharmaceutical composition is formed by adding sterile water or sterile saline solution (2 ml) to 500 mg of 7β-D-mandelamido-3-(1-ethoxyhydroxyphosphinylmethyltetrazol-5-ylthiomethyl)-3-cephem-4-carboxylic acid disodium salt. A unit dose is administered intramuscularly to a subject infected with an organism susceptible to the compound as noted herebefore every 4 to 6 hours. Intravenous or drip administration is also similarly used.

Similarly, pharmaceutical compositions of the other compounds of this invention may be prepared.

What is claimed is:
1. An antibacterial compound of the formula:

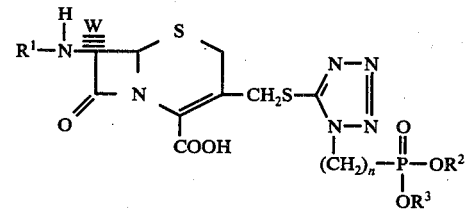

in which:
 W is hydrogen or methoxy;
 $R^1$ is a pharmaceutically acceptable acyl group known as a 7-substituent in the cephalosporin art;
 $R^2$ and $R^3$ are each hydrogen or alkyl of from one to four carbon atoms; and
 n is 1 to 5,
 or a non-toxic pharmaceutically acceptable salt or hydrate thereof.
2. A compound according to claim 1 in which $R^1$ is selected from the group consisting of:

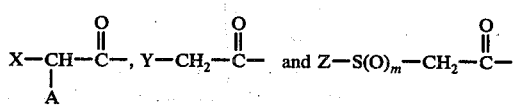

where:

X is thienyl, phenyl or phenyl monosubstituted with hydroxy, hydroxymethyl, formamido or ureido;
A is NH$_2$, OH, COOH, SO$_3$H or formyloxy;
Y is cyano, sydnone, thienyl, pyridone, tetrazolyl or aminomethylphenyl,
Z is methyl, trifluoromethyl, trifluoroethyl, pyridyl or cyanomethyl; and
m is 0 to 2.

3. A compound according to claim 2 in which R$^1$ is

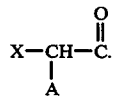

4. A compound according to claim 3 in which n is 1.
5. A compound according to claim 4 in which R$^2$ and R$^3$ are hydrogen.
6. A compound according to claim 4 in which one of R$^2$ and R$^3$ is alkyl and the other is hydrogen.
7. A compound according to claim 4 in which R$^2$ and R$^3$ are alkyl.
8. A compound according to claim 4 in which X is phenyl or hydroxyphenyl and A is NH$_2$ or OH.
9. A compound according to claim 8 in which R$^2$ and R$^3$ are each ethyl or hydrogen.
10. A compound according to claim 9 in which W is hydrogen.
11. A compound according to claim 9 in which W is methoxy.
12. A compound according to claim 10, said compound being 7β-mandelamido-3-(1-diethoxyphosphinylmethyltetrazol-5-ylthiomethyl)-3-cephem-4-carboxylic acid.
13. A compound according to claim 10, said compound being 7β-mandelamido-3-(1-ethoxyhydroxyphosphinylmethyltetrazol-5-ylthiomethyl)-3-cephem-4-carboxylic acid.
14. A compound according to claim 10, said compound being 7β-mandelamido-3-(1-phosphonomethyltetrazol-5-ylthiomethyl)-3-cephem-4-carboxylic acid.
15. A compound according to claim 10, said compound being 7β-(α-aminophenylacetamido)-3-(1-ethoxyhydroxyphosphinylmethyltetrazol-5-ylthiomethyl)-3-cephem-4-carboxylic acid.
16. A compound according to claim 10, said compound being 7β-(α-amino-4-hydroxyphenylacetamido)-3-(1-ethoxyhydroxyphosphinylmethyltetrazol-5-ylthiomethyl)-3-cephem-4-carboxylic acid.
17. A compound according to claim 10, said compound being 7β-mandelamido-3-(1-diethoxyphosphinylmethyltetrazol-5-ylthiomethyl)-3-cephem-4-carboxylic acid sodium salt.
18. A compound according to claim 10, said compound being 7β-mandelamido-3-(1-ethoxyhydroxyphosphinylmethyltetrazol-5-ylthiomethyl)-3-cephem-4-carboxylic acid disodium salt.
19. A compound according to claim 10, said compound being 7β-mandelamido-3-(1-phosphonomethyltetrazol-5-ylthiomethyl)-3-cephem-4-carboxylic acid disodium salt.
20. A compound according to claim 11, said compound being 7β-mandelamido-7α-methoxy-3-(1-phosphonomethyltetrazol-5-ylthiomethyl)-3-cephem-4-carboxylic acid.
21. A compound according to claim 11, said compound being 7β-(α-aminophenylacetamido)-7α-methoxy-3-(1-ethoxyhydroxyphosphinylmethyltetrazol-5-ylthiomethyl)-3-cephem-4-carboxylic acid.
22. A compound according to claim 11, said compound being 7β-mandelamido-7α-methoxy-3-(1-diethoxyphosphinylmethyltetrazol-5-ylthiomethyl)-3-cephem-4-carboxylic acid.
23. A compound according to claim 11, said compound being 7β-mandelamido-7α-methoxy-3-(1-ethoxyhydroxyphosphinylmethyltetrazol-5-ylthiomethyl)-3-cephem-4-carboxylic acid.
24. A compound according to claim 2 in which R$^1$ is

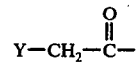

25. A compound according to claim 24 in which n is 1.
26. A compound according to claim 25 in which R$^2$ and R$^3$ are hydrogen.
27. A compound according to claim 25 in which one of R$^2$ and R$^3$ is alkyl and the other is hydrogen.
28. A compound according to claim 25 in which R$^2$ and R$^3$ are alkyl.
29. A compound according to claim 25 in which R$^2$ and R$^3$ are each ethyl or hydrogen.
30. A compound according to claim 29 in which W is hydrogen.
31. A compound according to claim 29 in which W is methoxy.
32. A compound according to claim 30, said compound being 7β-(2-thienylacetamido)-3-(1-ethoxyhydroxyphosphinylmethyltetrazol-5-ylthiomethyl)-3-cephem-4-carboxylic acid.
33. A compound according to claim 30, said compound being 7β-(1-tetrazolylacetamido)-3-(1-ethoxyhydroxyphosphinylmethyltetrazol-5-ylthiomethyl)-3-cephem-4-carboxylic acid.
34. A compound according to claim 30, said compound being 7β-(2-aminomethylphenylacetamido)-3-(1-ethoxyhydroxyphosphinylmethyltetrazol-5-ylthiomethyl)-3-cephem-4-carboxylic acid.
35. A compound according to claim 31, said compound being 7α-methoxy-7β-(2-thienylacetamido)-3-(1-ethoxyhydroxyphosphinylmethyltetrazol-5-ylthiomethyl)-3-cephem-4-carboxylic acid.
36. A compound according to claim 2 in which R$^1$ is

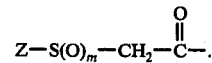

37. A compound according to claim 36 in which n is 1.
38. A compound according to claim 37 in which R$^2$ and R$^3$ are hydrogen.
39. A compound according to claim 37 in which one of R$^2$ and R$^3$ is alkyl and the other is hydrogen.
40. A compound according to claim 37 in which R$^2$ and R$^3$ are alkyl.
41. A compound according to claim 37 in which R$^2$ and R$^3$ are each ethyl or hydrogen.
42. A compound according to claim 41 in which W is hydrogen.
43. A compound according to claim 41 in which W is methoxy.

44. A compound according to claim 42, said compound being 7β-cyanomethylthioacetamido-3-(1-ethoxyhydroxyphosphinylmethyltetrazol-5-ylthiomethyl)-3-cephem-4-carboxylic acid.

45. A compound according to claim 42, said compound being 7β-trifluoromethylthioacetamido-3-(1-ethoxyhydroxyphosphinylmethyltetrazol-5-ylthiomethyl)-3-cephem-4-carboxylic acid.

46. A compound according to claim 43, said compound being 7α-methoxy-7β-trifluoromethylthioacetamido-3-(1-ethoxyhydroxyphosphinylmethyltetrazol-5-ylthiomethyl)-3-cephem-4-carboxylic acid.

47. A pharmaceutical composition having anti-bacterial activity comprising a compound as claimed in claim 1 and a pharmaceutically acceptable carrier therefor.

48. A pharmaceutical composition comprising a compound as claimed in claim 12 and a pharmaceutically acceptable carrier therefor.

49. A pharmaceutical composition comprising a compound as claimed in claim 13 and a pharmaceutically acceptable carrier therefor.

50. A pharmaceutical composition comprising a compound as claimed in claim 14 and a pharmaceutically acceptable carrier therefor.

51. A method of treating bacterial infections comprising administering internally by injection to an infected or susceptible warm-blooded animal an anti-bacterially effective but nontoxic dose of a compound as claimed in claim 1.

52. The method of claim 51 in which the compound is 7β-mandelamido-3-(1-phosphonomethyltetrazol-5-ylthiomethyl)-3-cephem-4-carboxylic acid.

53. The method of claim 51 in which the compound is 7β-mandelamido-3-(1-ethoxyhydroxyphosphinylmethyltetrazol-5-ylthiomethyl)-3-cephem-4-carboxylic acid.

54. The method of claim 51 in which the compound is 7β-mandelamido-3-(1-diethoxyphosphinylmethyltetrazol-5-ylthiomethyl)-3-cephem-4-carboxylic acid.

55. A compound according to claim 10, said compound being 7β-D-mandelamido-3-(1-diethoxyphosphinylmethyltetrazol-5-ylthiomethyl)-3-cephem-4-carboxylic acid.

56. A compound according to claim 10, said compound being 7β-D-mandelamido-3-(1-ethoxyhydroxyphosphinylmethyltetrazol-5-ylthiomethyl)-3-cephem-4-carboxylic acid.

57. A compound according to claim 10, said compound being 7β-D-mandelamido-3-(1-phosphonomethyltetrazol-5-ylthiomethyl)-3-cephem-4-carboxylic acid.

* * * * *